(12) United States Patent
Jiang

(10) Patent No.: US 12,295,769 B2
(45) Date of Patent: May 13, 2025

(54) IMAGE PRESENTATION METHOD AND SYSTEM FOR MEDICAL IMAGING, IMAGING SYSTEM, AND STORAGE MEDIUM

(71) Applicant: Siemens Healthcare GmbH, Erlangen (DE)

(72) Inventor: Peng Cheng Jiang, Shenzhen (CN)

(73) Assignee: Siemens Healthineers AG, Erlangen (DE)

( * ) Notice: Subject to any disclaimer, the term of this patent is extended or adjusted under 35 U.S.C. 154(b) by 436 days.

(21) Appl. No.: 17/703,302

(22) Filed: Mar. 24, 2022

(65) Prior Publication Data
US 2022/0304640 A1 Sep. 29, 2022

(30) Foreign Application Priority Data
Mar. 26, 2021 (CN) .......................... 202110324848.X

(51) Int. Cl.
*A61B 6/00* (2024.01)
*A61B 6/46* (2024.01)
*G06T 7/564* (2017.01)
*G16H 30/40* (2018.01)

(52) U.S. Cl.
CPC .............. *A61B 6/461* (2013.01); *G06T 7/564* (2017.01); *G16H 30/40* (2018.01); *G06T 2207/20224* (2013.01); *G06T 2207/30101* (2013.01)

(58) Field of Classification Search
CPC .................. A61B 6/461; G06T 7/564; G06T 2207/20224; G06T 2207/30101; G16H 30/40
See application file for complete search history.

(56) References Cited

U.S. PATENT DOCUMENTS

| 5,056,524 A | 10/1991 | Oe |
| 9,433,392 B2 * | 9/2016 | Ohishi ................. A61B 6/5211 |
| 2015/0161782 A1 | 6/2015 | Mohr et al. |
| 2018/0260998 A1 * | 9/2018 | Ohishi .................... G06T 15/08 |

(Continued)

FOREIGN PATENT DOCUMENTS

| CN | 104700397 A | 6/2015 |
| CN | 110490835 A | 11/2019 |

(Continued)

*Primary Examiner* — Khai M Nguyen
(74) *Attorney, Agent, or Firm* — Banner & Witcoff Ltd.

(57) ABSTRACT

The present disclosure is directed to techniques for medical imaging image presentation. The techniques include obtaining, for a target area including a first target, an image of the target area that is taken without a contrast agent and an image of the target area that is taken with a contrast agent. The techniques also include subtracting the image that is taken with a contrast agent from the image that is taken without a contrast agent to obtain a subtraction image; extracting a contour of a second target from the subtraction image, to obtain a contour image of the second target; and registering, based on a same marker, the contour image of the second target and a currently-acquired (e.g. real-time) image, and then displaying the images in a superimposed manner. The technical solutions in the embodiments of the present disclosure improve the efficiency of treatment based on radiological images.

20 Claims, 3 Drawing Sheets

201 — Obtain an image with and without a contrast agent for a target area

202 — Subtract the image obtained with the contrast agent from the image obtained without the contrast agent to obtain a subtraction image 203 — Extract a contour of a second target from the subtraction image to obtain a contour image of the second target 204 — Register the contour image of the second target and a currently-acquired real-time image based on the same marker and display the registered images in a superimposed manner

(56) References Cited

U.S. PATENT DOCUMENTS

2019/0172205 A1\* 6/2019 Mao ...................... G06T 7/0014
2019/0347793 A1 11/2019 Breininger et al.

FOREIGN PATENT DOCUMENTS

| DE | 102018211477 B4 \* | 8/2024 | ............ A61B 34/10 |
| JP | 2004265292 A \* | 9/2004 | |
| JP | 2006034355 A \* | 2/2006 | |
| JP | 2019181213 A | 10/2019 | |

\* cited by examiner

IMAGE PRESENTATION METHOD AND SYSTEM FOR MEDICAL IMAGING, IMAGING SYSTEM, AND STORAGE MEDIUM

CROSS-REFERENCE TO RELATED APPLICATIONS

The present application claims the benefit of the filing date of China patent application no. CN 202110324848.X, filed on Mar. 26, 2021, the contents of which are incorporated herein by reference in their entirety.

TECHNICAL FIELD

The disclosure relates to the field of medical treatment and, in particular, to an image presentation method and system for medical imaging, an imaging system, and a computer-readable storage medium.

BACKGROUND

An aneurysm is a local pathologic bulge in the wall of an artery, such as an intracranial aneurysm which is a local abnormal ballooning in a cerebral artery. With an incidence rate of about 5% to 10%, the intracranial aneurysm is a disease that causes a very high rate of death and disability among middle-aged and young patients. Therefore, once it is diagnosed, necessary treatment should be provided. With the development of technical methods and materials, and the accumulation of experience of neurointerventionalists, endovascular treatment has become the first choice of treating intracranial aneurysms.

Endovascular treatment of aneurysms involves delivering a microcatheter into an aneurysm, and then occluding the aneurysm with materials such as a coil and a medical glue, thereby preventing bleeding and relapse of the aneurysm. In some treatments, such as those of a wide-necked aneurysm or a fusiform aneurysm, a technique of stent-assisted coiling may be used for embolization of aneurysms. A stent is a tubular supportive device which may be delivered into a blood vessel by using a specially-made delivery system that is attached to the inner wall of the blood vessel. Placing a stent in advance facilitates tightly packing an aneurysm and prevents a coil from protruding into a parent artery. There are two modes of operation for the technique of stent-assisted coiling. The first is placing a stent across an opening of an aneurysm, then inserting a microcatheter into the cavity of the aneurysm through the mesh of the stent, delivering a coil to occlude the aneurysm, and withdrawing the microcatheter in the end. The second is inserting a microcatheter into the cavity of an aneurysm, and then placing a stent across an opening of the aneurysm, delivering a coil through the microcatheter to embolize the aneurysm, and withdrawing the microcatheter in the end. During the above process, the stent placed in advance is sometimes not completely eluting, and will continue eluting after the aneurysm embolization is completed.

During endovascular treatment, radiological images are required for guidance. In addition, because a contrast between a blood vessel and its surrounding tissues is low, an acquired real-time image cannot be directly used for guidance of embolization. In such a case, an extra blood vessel route image for guidance needs to be made. For example, generally, by using a technique of digital subtraction angiography (DSA), an image that is taken with a contrast agent is subtracted from an image that is taken without a contrast agent to obtain a blood vessel subtraction image. The blood vessel subtraction image is highlighted to obtain the blood vessel route image, and the blood vessel route image is superimposed onto the real-time image for guidance of embolization. However, a vision of a stent inside a blood vessel may be weakened in or even removed from the above blood vessel subtraction image during subtraction thereof, and consequently an image of the stent is also weakened in or removed from the blood vessel route image obtained by highlighting the blood vessel subtraction image.

As shown in FIG. 1, a rectangular box, that is, an area A in FIG. 1A, represents an area including the stent, but no image of the stent can be seen, which is unfavorable for treatment in terms of aneurysm embolization using the technique of stent-assisted coiling. As a result, doctors can place a coil 11 only under the guidance of a blood vessel route image as shown in FIG. 1B, and observe a status of a stent on another reference monitor. Application which requires elution of the stent after aneurysm embolization requires an additional blood vessel route image for guiding the elution of the stent to be made after the aneurysm embolization is completed. It can be seen that this process takes a great deal of time and causes a waste of contrast agents and an increase in X-ray dosage.

SUMMARY

In view of this, embodiments of the present disclosure provide an image presentation method for medical imaging in an aspect, and an image presentation system for medical imaging, an image imaging system, and a computer-readable storage medium in other aspects, to improve the efficiency of treatment based on radiological images.

The image presentation method for medical imaging provided in an embodiment of the present disclosure includes: obtaining, for a target area including a first target, an image of the target area that is taken without a contrast agent and an image of the target area that is taken with a contrast agent; subtracting the image that is taken with a contrast agent from the image that is taken without a contrast agent, to obtain a subtraction image; extracting a contour of a second target from the subtraction image, to obtain a contour image of the second target; and registering, based on a same marker, the contour image of the second target and a currently-acquired (e.g. real-time) image, and then displaying the images in a superimposed manner.

In one realization, the step of subtracting the image that is taken with a contrast agent from the image that is taken without a contrast agent, to obtain a subtraction image includes: performing a difference calculation on the image that is taken with a contrast agent and the image that is taken without a contrast agent by using a differential algorithm for digital images, to obtain the subtraction image.

In one realization, the step of extracting a contour of a second target from the subtraction image includes: performing detection and segmentation on the subtraction image by using an edge detection algorithm and an image segmentation algorithm to obtain the contour of the second target.

In one realization, the step of registering, based on a same marker, the contour of the second target and a currently-acquired (e.g. real-time) image, and then displaying the images in a superimposed manner includes: determining, based on the image that is taken with a contrast agent, two reference points on the contour of the second target and one mark point on the marker, and calculating a position relationship between the two reference points and the mark point; and determining, from each currently-acquired (e.g.

real-time) image, a corresponding mark point on the same marker, registering the contour image of the second target and the currently-acquired (e.g. real-time) image based on the position relationship, and displaying the two images in a superimposed manner by using a pixel translation algorithm; or determining, from a single currently-acquired image, a corresponding mark point on the same marker, registering the contour image of the second target and the single image based on the position relationship, and superimposing, based on a relationship of the registration, the contour image of the second target separately onto the single image and each currently-acquired (e.g. real-time) image acquired thereafter for displaying.

In one realization, the method further includes: receiving a shift instruction of a user for the contour image of the second target that is superimposed onto the currently-acquired (e.g. real-time) image for displaying, and adjusting a position of the contour image of the second target according to the shift instruction.

In one realization, the method further includes: receiving a reset instruction of the user for the contour image of the second target that is superimposed onto the currently-acquired (e.g. real-time) image for displaying, and returning the contour image of the second target to an initial superimposition position according to the reset instruction.

The image presentation system for medical imaging provided in an embodiment of the present disclosure includes: a first unit configured to obtain, for a target area including an aneurysm, an image of the target area that is taken without a contrast agent and an image of the target area that is taken with a contrast agent; a second unit configured to subtract the image that is taken with a contrast agent from the image that is taken without a contrast agent, to obtain a subtraction image; a third unit configured to extract a contour of a second target from the subtraction image, to obtain a contour image of the second target; and a fourth unit configured to register, based on a same marker, the contour image of the second target and a currently-acquired (e.g. real-time) image, and then display the images in a superimposed manner.

In one realization, the second unit performs a difference calculation on the image that is taken with a contrast agent and the image that is taken without a contrast agent by using a differential algorithm for digital images, to obtain the subtraction image.

In one realization, the third unit performs detection and segmentation on the subtraction image by using an edge detection algorithm and an image segmentation algorithm, to obtain the contour of the second target.

In one realization, the fourth unit further determines, based on the image that is taken with a contrast agent, two reference points on the contour of the second target and one mark point on the marker, and calculates a position relationship between the two reference points and the mark point; and the fourth unit then determines, from each currently-acquired (e.g. real-time) image, a corresponding mark point on the same marker, registers the contour image of the second target and the currently-acquired (e.g. real-time) image based on the position relationship, and displays the two images in a superimposed manner by using a pixel translation algorithm; or, the fourth unit determines, from a single currently-acquired image, a corresponding mark point on the same marker, registers the contour image of the second target and the single image based on the position relationship, and superimposes, based on a relationship of the registration, the contour image of the second target separately onto the single image and each currently-acquired (e.g. real-time) image acquired thereafter.

The image presentation system for medical imaging provided in an embodiment of the present disclosure includes: at least one memory and at least one processor, where the at least one memory is configured to store a computer program; and the at least one processor is configured to invoke the computer program stored in the at least one memory, to perform the image presentation method for medical imaging according to any one of the above realizations.

The imaging system provided in an embodiment of the present disclosure includes a medical angiography X-ray machine and the image presentation system for medical imaging according to any one of the above realizations.

The computer-readable storage medium provided in an embodiment of the present disclosure has a computer program stored thereon, where the computer program is capable of being executed by a processor to implement the image presentation method for medical imaging according to any one of the above realizations.

It can be seen from the above solutions that in the embodiments of the present disclosure, the contour image of the second target, such as a blood vessel contour image, which is superimposed onto the currently-acquired (e.g. real-time) image for displaying does not cover images of other objects, such as an image of a stent, in the currently-acquired (e.g. real-time) image, such that both the contour image of the second target for guidance, such as a blood vessel contour image, and an image of another object, for example, an image of a stent, can be displayed on a same image, and there is no need to display the contour image of the second target such as a blood vessel route image, and an image of another object such as an image of a stent, separately on two display screens, thereby improving the efficiency of treatment based on radiological images, for example, endovascular treatment of aneurysms.

In addition, application which requires elution of the stent after aneurysm embolization requires no additional blood vessel route image for guiding the elution of the stent to be made because an image of the stent is displayed in the currently-acquired (e.g. real-time) image throughout, thereby reducing contrast agent and X-ray dosage.

In addition, images superimposed through currently-acquired (e.g. real-time) registration can make display more accurate, and images superimposed through one-time registration can reduce the amount of computation.

Moreover, providing a function of manually adjusting or resetting a superimposition position can allow a superimposition effect to be adjusted based on actual situations, thereby enhancing the applicability of the system.

BRIEF DESCRIPTION OF THE DRAWINGS/FIGURES

The above and other features and advantages of the present disclosure will be more apparent to those of ordinary skill in the art from the detailed description of preferred embodiments of the present disclosure with reference to the accompanying drawings, in which.

Figure 1A:
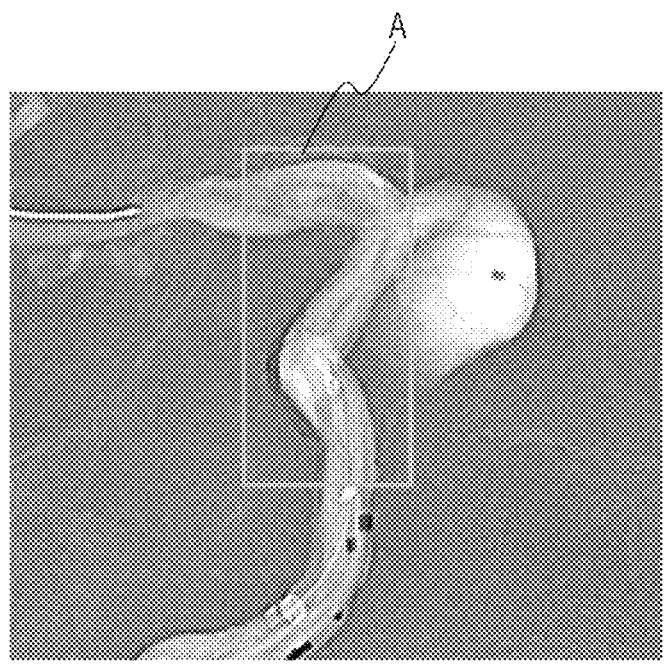
FIG. 1A illustrates a schematic diagram of a currently-acquired (e.g. real-time) image with a blood vessel route image superimposed thereon.
Figure 1B:
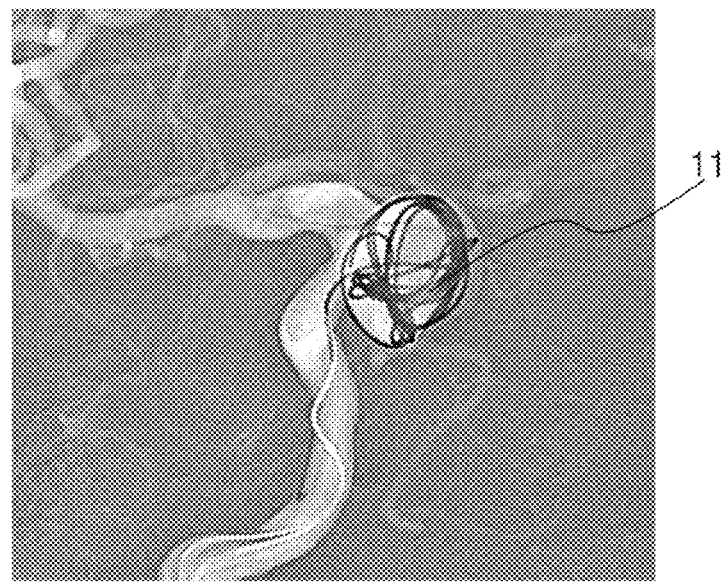
FIG. 1B illustrates a schematic diagram for placement of a coil under the guidance of the blood vessel route image.

Reference numerals in the accompanying drawings are as follows:

| Reference numeral | Meaning |
|---|---|
| 11 | Coil |
| 201 to 204 | Step |
| 301 | First unit |
| 302 | Second unit |
| 303 | Third unit |
| 304 | Fourth unit |
| 41 | Memory |
| 42 | Processor |
| 43 | Display |
| 44 | Bus |

DETAILED DESCRIPTION

In embodiments of the present disclosure, to improve the efficiency of endovascular treatment of aneurysms by displaying a blood vessel guidance image and an image of a stent on a same image, it is considered that a blood vessel route image obtained by highlighting a blood vessel subtraction image is not directly used as the blood vessel guidance image, instead, a blood vessel contour image is used as the blood vessel guidance image. When superimposed onto a currently-acquired (e.g. real-time) image, a blood vessel contour does not cover an image of the stent in the currently-acquired (e.g. real-time) image. In addition, the same method may also be used for some other treatments based on radiological images, for example, treatment of polyps in digestive tracts.

In order to make the objectives, technical solutions, and advantages of the present disclosure more apparent, the present disclosure will be described in further detail by way of embodiments hereinafter.

Figure 2:
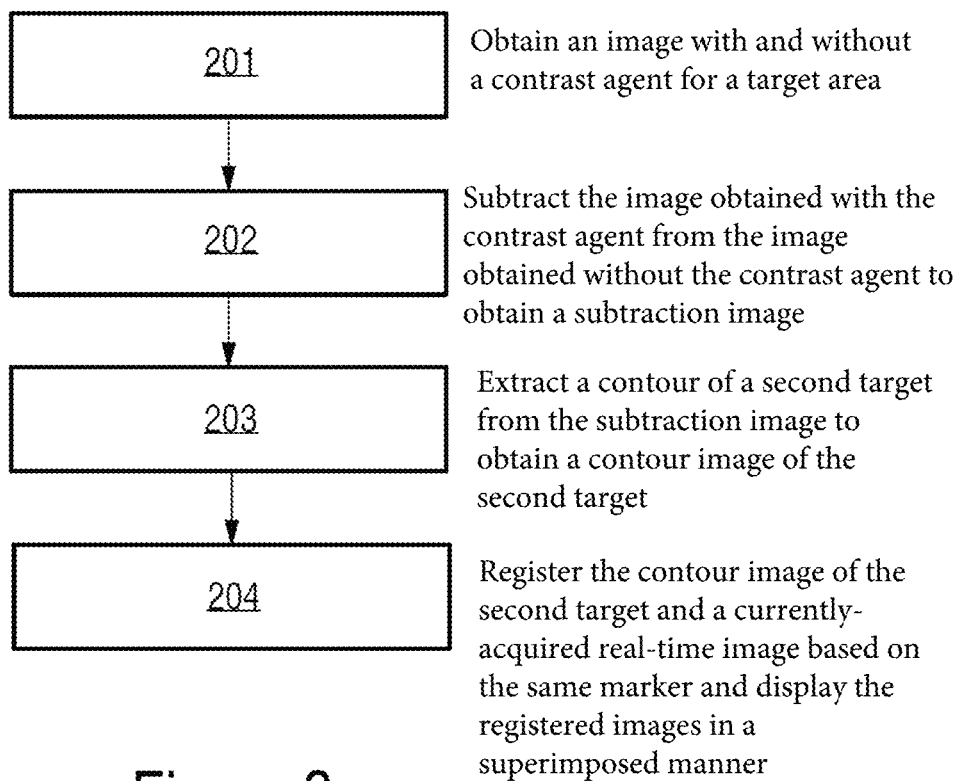
FIG. 2 illustrates an exemplary flowchart of an image presentation method for medical imaging according to an embodiment of the present disclosure.

FIG. 2 illustrates an exemplary flowchart of an image presentation method for medical imaging according to an embodiment of the present disclosure. As shown in FIG. 2, the method may include the steps as follows.

Step 201: An image that is taken without a contrast agent and an image that is taken with a contrast agent are obtained for a target area including a first target.

In an example, the first target may be an aneurysm. For example, for a target area including the aneurysm, an image of the target area that is taken without a contrast agent and an image of the target area that is taken with a contrast agent are separately obtained. The contrast agent is injected into a blood vessel. Correspondingly, an X-ray equipment used to acquire images may be a medical angiography X-ray machine.

In another example, the first target may be a polyp of intestine, and in this case, the contrast agent is injected into an intestine.

Step 202: The image that is taken with a contrast agent is subtracted from the image that is taken without a contrast agent, to obtain a subtraction image.

During specific implementation, a plurality of methods may be used for image subtraction operations. For example, a difference calculation may be performed on the image that is taken with a contrast agent and the image that is taken without a contrast agent by using a differential algorithm for digital images, to obtain the subtraction image.

In an example, the subtraction image may be a blood vessel subtraction image. In another example, the subtraction image may be an intestine subtraction image.

Step 203: A contour of a second target is extracted from the subtraction image, to obtain a contour image of the second target.

During specific implementation, there may be a plurality of methods for extracting the contour of the second target. For example, detection and segmentation may be performed on the blood vessel subtraction image by using an edge detection algorithm and an image segmentation algorithm, to obtain the contour of the second target.

In an example, the second target may be a blood vessel. In another example, the second target may be an intestine.

Step 204: The contour image of the second target and a currently-acquired (e.g. real-time) image are registered based on a same marker, and then displayed in a superimposed manner. In other examples, step 204 could be separated into two steps including one step for the act of registering and the other step for the act of displaying.

The marker may be a relatively static object, such as bones, in an image that can show up in both a common X-ray image and an augmented image.

During example implementations, there may be a plurality of methods for registration. For example, two reference points (such as branch nodes) on the contour of the second target and one mark point on the marker may be determined based on the image that is taken with a contrast agent, and a position relationship between the two reference points and the mark point may be calculated. Then, a corresponding mark point on the same marker is determined from each currently-acquired (e.g. real-time) image, the contour image of the second target and the currently-acquired image are registered based on the position relationship, and the two images may be subjected to registration (e.g. in real time) and then displayed in a superimposed manner by using a pixel translation algorithm. Alternatively, a corresponding mark point on the same marker may be determined from a single currently-acquired image, the contour image of the second target and the single image are registered based on the position relationship, and the contour image of the second target is superimposed, based on a relationship of the registration, separately onto the single image and each currently-acquired (e.g. real-time) image acquired thereafter. That is, the process of registration may be real-time registration, or may be one-time registration.

As such, for endovascular treatment of aneurysms, both the blood vessel contour image for guidance and an image of a stent can be displayed on a same image, without the need for separate display of a blood vessel route image and the image of the stent on two display screens, thereby improving the efficiency of endovascular treatment of aneurysms. In addition, application which requires elution of the stent after aneurysm embolization requires no additional blood vessel route image for guiding the elution of the stent to be made because an image of the stent is displayed in the currently-acquired (e.g. real-time) image throughout, thereby reducing contrast agent and X-ray dosage. Other treatments based on radiological images, for example, resection of a polyp inside an intestine, do not necessarily require a stent, but an intestine contour image may still be used as a guidance image.

In this embodiment, positions of the system and a patient need to remain unchanged.

In this embodiment, the currently-acquired (e.g. real-time) image after the superimposition may be displayed on any suitable type of display screen, e.g. in real time. The display may refer to a screen for displaying currently-acquired (e.g. real-time) images/a display or a display screen/a partial area of a display.

In addition, in this embodiment, a user is allowed to adjust a position of the contour image of the second target that is to be superimposed onto the currently-acquired (e.g. real-time) image for displaying. For example, if the user thinks that an initial superimposition position after automatic superimposition made by the system in step 204 is not very accurate, the user can be allowed to perform operations for a position change of the contour image of the second target, such as moving same up and down, and moving same to the left and right. Correspondingly, in this embodiment the method may further include: providing the user with a function of adjusting a position of the contour image of the second target that is superimposed onto the currently-acquired (e.g. real-time) image for displaying, receiving a shift instruction of the user for the contour image of the second target that is superimposed onto the currently-acquired (e.g. real-time) image for displaying, and adjusting the position of the contour image of the second target according to the shift instruction. In addition, if the user is not satisfied with a position after the manual adjustment, in this embodiment, a function of returning to the initial superimposition position may be further provided to the user. Correspondingly, a reset instruction of the user for the contour image of the second target that is superimposed onto the currently-acquired (e.g. real-time) image for displaying may be received, and the contour image of the second target may be returned to the initial superimposition position according to the reset instruction.

The image presentation method in interventional treatment according to this embodiment of the present disclosure has been described above in detail, and an image presentation system in interventional treatment according to an embodiment of the present disclosure will be described below in detail. The image presentation system in interventional treatment according to this embodiment of the present disclosure may be used to implement the image presentation method in interventional treatment according to the embodiments of the present disclosure. For details not disclosed in the system embodiment of the present disclosure, reference may be made to the corresponding description in the method embodiment of the present disclosure, and the details are not repeated herein.

Figure 3:
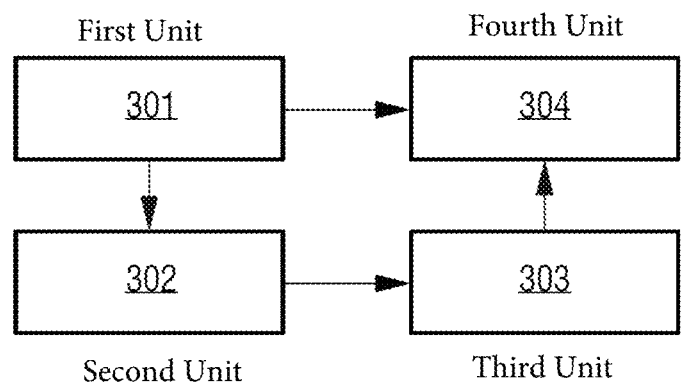
FIG. 3 illustrates an exemplary structural diagram of an image presentation system for medical imaging according to an embodiment of the present disclosure.

FIG. 3 is an exemplary structural diagram of an image presentation system for medical imaging according to an embodiment of the present disclosure. As shown in FIG. 3, the system may include: a first unit 301, a second unit 302, a third unit 303, and a fourth unit 304.

The first unit 301 (e.g. image acquisition circuitry) is configured to obtain, for a target area including a first target, an image of the target area that is taken without a contrast agent and an image of the target area that is taken with a contrast agent.

The second unit 302 (e.g. difference image acquisition circuitry) is configured to subtract the image that is taken with a contrast agent from the image that is taken without a contrast agent to obtain a subtraction image.

During an example implementation, the second unit 302 may perform a difference calculation on the image that is taken with a contrast agent and the image that is taken without a contrast agent by using a differential algorithm for digital images, to obtain the subtraction image.

The third unit 303 (e.g. contour extraction circuitry) is configured to extract a contour of a second target from the subtraction image, to obtain a contour image of the second target.

During an example implementation, the third unit 303 may perform detection and segmentation on the subtraction image by using an edge detection algorithm and an image segmentation algorithm, to obtain the contour of the second target.

The fourth unit 304 (e.g. registration circuitry) is configured to register, based on a same marker, the contour image of the second target and a currently-acquired (e.g. real-time) image, and then display the images in a superimposed manner. In other examples, the fourth unit 304 could be replaced with two units (e.g. a registration circuitry and any suitable type of display) to be configured respectively for the acts of registering and displaying.

During an example implementation, the fourth unit 304 may further determine, based on the image that is taken with a contrast agent, two reference points on the contour of the second target and one mark point on the marker, and calculate a position relationship between the two reference points and the mark point; and the fourth unit may then determine, from each currently-acquired (e.g. real-time) image, a corresponding mark point on the same marker, register the contour image of the second target and the currently-acquired (e.g. real-time) image based on the position relationship, and display the two images in a superimposed manner by using a pixel translation algorithm; or, the fourth unit may determine, from a single currently-acquired image, a corresponding mark point on the same marker, register the contour image of the second target and the single image based on the position relationship, and superimpose, based on a relationship of the registration, the contour image of the second target separately onto the single image and each currently-acquired (e.g. real-time) image acquired thereafter.

In one realization, the fourth unit 304 may further be configured to receive a shift instruction of a user for the contour image of the second target that is superimposed onto the currently-acquired (e.g. real-time) image for displaying, and adjust a position of the contour image of the second target according to the shift instruction.

In one realization, the fourth unit 304 is further configured to receive a reset instruction of the user for the contour image of the second target that is superimposed onto the currently-acquired (e.g. real-time) image for displaying, and return the contour image of the second target to an initial superimposition position according to the reset instruction.

Figure 4:
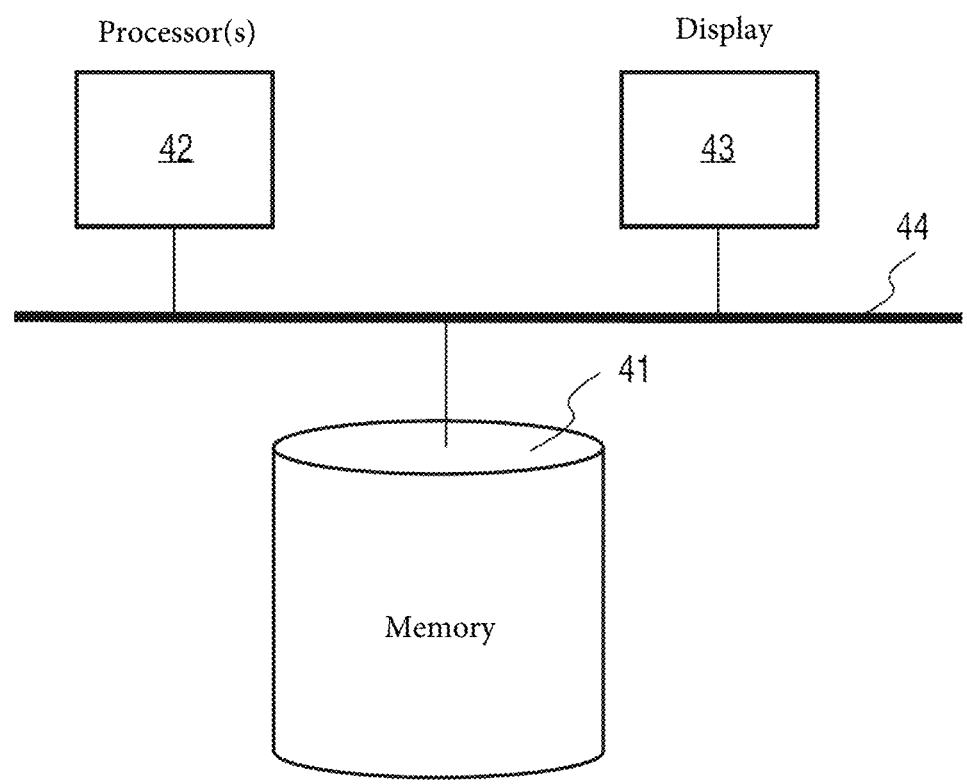
FIG. 4 illustrates an exemplary structural diagram of another image presentation system for medical imaging according to an embodiment of the present disclosure.

FIG. 4 is a schematic structural diagram of another image presentation system in endovascular treatment of aneurysms according to an embodiment of the present disclosure. As shown in FIG. 4, the system may include: at least one memory 41, at least one processor 42, and at least one display 43. In addition, some other components, such as a communication port, may further be included. The components communicate with each other by a bus 44.

The at least one memory 41 is configured to store a computer program. In one realization, the computer program may be understood as including various modules of the image presentation system in endovascular treatment of aneurysms shown in FIG. 3. In addition, the at least one memory 41 may further store an operating system, etc. The operating system includes, but is not limited to: an Android operating system, a Symbian operating system, a Windows operating system, a Linux operating system, etc.

The at least one display 43 is configured to display the image that is taken without a contrast agent, the image that is taken with a contrast agent, the contour image of the second target, the currently-acquired (e.g. real-time) image superimposed for displaying, etc.

The at least one processor 42 is configured to invoke (e.g. execute) the computer program stored in the at least one memory 41 to perform the image presentation method for medical imaging according to the embodiments of the present disclosure. The processor 42 may be a CPU, a processing unit/module, an ASIC, a logic module or a programmable gate array, etc. The processor may perform data receiving and sending by using the communication port.

An embodiment of the present disclosure further provides an imaging system, which includes an X-ray equipment, for example, a medical angiography X-ray machine, and the image presentation system for medical imaging according to any one of the above realizations.

It is noted that not all the steps and modules in the flows and structural diagrams described above are necessary, and some steps or modules may be omitted according to practical requirements. The division of various modules is merely function division adopted for ease of description. In actual implementation, one module may be implemented by a plurality of modules, respectively, and functions of a plurality of modules may also be implemented by the same module. These modules may be located in the same device, or may be located in different devices.

It can be understood that hardware modules in the various realizations described above may be implemented mechanically and/or electrically. For example, one hardware module may include a specifically designed permanent circuit or logic device (for example, a dedicated processor such as an FPGA or an ASIC) for accomplishing specific operations. The hardware module may also include a programmable logic device or circuit (for example, including a general-purpose processor or other programmable processors), which is configured temporarily by software, for performing specific operations. Whether the hardware module is implemented in a mechanical manner, by using a dedicated permanent circuit, or by using a temporarily configured circuit (for example, configured by software) may be decided according to costs and time.

In addition, an embodiment of the present disclosure further provides a computer-readable storage medium having a computer program stored thereon, where the computer program can be executed by a processor, to implement the image presentation method for medical imaging according to the embodiments of the present disclosure. Specifically, a system or an apparatus with a storage medium may be provided, where software program codes for implementing the functions of any one of the realizations of the above embodiments are stored on the storage medium, and a computer (or a CPU or an MPU) of the system or apparatus is caused to read out and execute the program codes stored in the storage medium. Moreover, an operating system operating on a computer may be caused to accomplish some or all of the actual operations based on an instruction of the program codes. The program codes read out from the storage medium may be further written into a memory provided in an expansion board inserted into the computer or written into a memory provided in an expansion unit connected to the computer, and then a CPU, etc. installed on the expansion board or the expansion unit is caused to execute some or all of the actual operations based on the instruction of the program codes, thereby implementing the functions of any one of the above realizations. The realizations of the storage medium for providing the program codes comprise a floppy disk, a hard disk, a magnetic optical disc, an optical disc (e.g., CD-ROM, CD-R, CD-RW, DVD-ROM, DVD-RAM, DVD-RW and DVD+RW), a magnetic tape, a non-volatile memory card and an ROM. Optionally, the program codes may be downloaded from a server computer via a communication network.

It can be seen from the above solutions that in the embodiments of the present disclosure, the contour image of the second target, such as a blood vessel contour image, that is superimposed onto the currently-acquired (e.g. real-time) image for displaying does not cover images of other objects, such as an image of a stent, in the currently-acquired (e.g. real-time) image, such that both the contour image of the second target for guidance, such as a blood vessel contour image, and an image of another object, for example, an image of a stent, can be displayed on a same image, and there is no need to display the contour image of the second target such as a blood vessel route image, and an image of another object such as an image of a stent, separately on two display screens, thereby improving the efficiency of treatment based on radiological images, for example, endovascular treatment of aneurysms.

In addition, applications which require elution of the stent after aneurysm embolization requires no additional blood vessel route image for guiding the elution of the stent to be made because an image of the stent is displayed in the currently-acquired (e.g. real-time) image throughout, thereby reducing contrast agent and X-ray dosage.

In addition, images superimposed through e.g. real-time registration can make display more accurate, and images superimposed through one-time registration can reduce the amount of computation.

Moreover, providing a function of manually adjusting or resetting a superimposition position can allow a superimposition effect to be adjusted based on actual situations, thereby enhancing the applicability of the system.

The above description is illustrative of the preferred embodiments of the present disclosure and is not intended to limit the present disclosure. Any modifications, equivalent substitutions, improvements, etc. made within the spirit and principles of the present disclosure shall fall within the scope of protection of the present disclosure.

The various components described herein may be referred to as "modules" or "units." As noted above, such components may be implemented via any suitable combination of parts, components, hardware, and/or software components as applicable and/or known to achieve the intended respective functionality. This may include mechanical and/or electrical components, FPGAs, processors, processing circuitry, or other suitable hardware components configured to execute instructions or computer programs that are stored on a suitable computer readable medium. Regardless of the particular implementation, such units or modules when applicable and relevant may alternatively be referred to herein as "circuitry," "processors," or "processing circuitry."

What is claimed is:

1. An image presentation method for medical imaging, comprising:
    obtaining, for a target area including a first target, (i) a first image of the target area, which is taken without the use of a contrast agent in the target area, and (ii) a second image of the target area, which is taken with the use of a contrast agent in the target area;
    subtracting the second image from the first image to obtain a subtraction image;

extracting a contour of a second target from the subtraction image to obtain a contour image of the second target;
registering, based on a same marker, the contour image of the second target and a currently-acquired image; and
displaying the registered contour image of the second target and the currently-acquired image in a superimposed manner,
wherein the registering and the displaying the contour of the second target and the currently-acquired image comprise:
determining, based on the second image, two reference points on the contour of the second target and a mark point on the marker:
calculating a position relationship between the two reference points and the mark point; and
from each one of a set of currently-acquired images that includes the currently-acquired image:
determining a corresponding mark point on the same marker:
registering the contour image of the second target and a respective currently acquired image from among the set of currently-acquired images based on the position relationship; and
displaying the contour of the second target and the respective currently-acquired image in a superimposed manner using a pixel translation algorithm.

2. The image presentation method for medical imaging according to claim 1,
wherein the subtracting the second image from the first image to obtain the subtraction image comprises:
performing a difference calculation on the second image and the first image using a differential algorithm for digital images to obtain the subtraction image.

3. The image presentation method for medical imaging according to claim 1,
wherein the extracting the contour of the second target from the subtraction image comprises:
performing detection and segmentation on the subtraction image using an edge detection algorithm and an image segmentation algorithm to obtain the contour of the second target.

4. The image presentation method for medical imaging according to claim 1, further comprising:
receiving a shift instruction for the contour image of the second target that is superimposed onto the currently-acquired image; and
adjusting a position of the contour image of the second target according to the shift instruction.

5. The image presentation method for medical imaging according to claim 4, further comprising:
receiving a reset instruction for the contour image of the second target that is superimposed onto the currently-acquired image; and
returning the contour image of the second target to a predetermined superimposition position according to the reset instruction.

6. An image presentation system for medical imaging, comprising:
image acquisition circuitry configured to obtain, for a target area including a first target, a first image of the target area, which is taken without the use of a contrast agent in the target area, and a second image of the target area, which is taken with the use of the contrast agent in the target area;
difference image acquisition circuitry configured to subtract the second image from the first image to obtain a subtraction image;
contour extraction circuitry configured to extract a contour of a second target from the subtraction image to obtain a contour image of the second target;
registration circuitry configured to register, based on a same marker, the contour image of the second target and a currently-acquired image; and
a display configured to present the registered contour image of the second target and the currently-acquired image in a superimposed manner,
wherein the registration circuitry is further configured to;
determine, based on the second image, two reference points on the contour of the second target and a mark point on the marker:
calculate a position relationship between the two reference points and the mark point;
from each one of a set of currently-acquired images that includes the currently-acquired image:
determine a corresponding mark point on the same marker;
register the contour image of the second target and a respective currently-acquired image from among the set of currently-acquired images based on the position relationship; and
present the contour of the second target and the respective currently-acquired image in a superimposed manner using a pixel translation algorithm.

7. The image presentation system for medical imaging according to claim 6, wherein the difference image acquisition circuitry is configured to perform a difference calculation on the second image and the first image using a differential algorithm for digital images to obtain the subtraction image.

8. The image presentation system for medical imaging according to claim 6, wherein the contour extraction circuitry is configured to perform detection and segmentation on the subtraction image using an edge detection algorithm and an image segmentation algorithm to obtain the contour of the second target.

9. An image presentation system for medical imaging, comprising:
a memory configured to store a computer program; and
a processor configured to execute the computer program stored in the memory to cause the image presentation system to:
obtain, for a target area including a first target, (i) a first image of the target area, which is taken without the use of a contrast agent in the target area, and (ii) a second image of the target area, which is taken with the use of a contrast agent in the target area;
subtract the second image from the first image to obtain a subtraction image;
extract a contour of a second target from the subtraction image to obtain a contour image of the second target;
register, based on a same marker, the contour image of the second target and a currently-acquired image; and
display the registered contour image of the second target and the currently-acquired image in a superimposed manner,
wherein the processor is further configured to register and display the contour of the second target and the currently-acquired image by:

determining, based on the second image, two reference points on the contour of the second target and a mark point on the marker;

calculating a position relationship between the two reference points and the mark point;

from each one of a set of currently-acquired images that includes the currently-acquired image:

determining a corresponding mark point on the same marker;

registering the contour image of the second target and a respective currently-acquired image from among the set of currently-acquired images based on the position relationship; and presenting the contour of the second target and the respective currently-acquired image in a superimposed manner using a pixel translation algorithm.

10. The image presentation system of claim 9, wherein the image presentation systems is part of a medical angiography X-ray machine.

11. An image presentation method for medical imaging, comprising:

obtaining, for a target area including a first target, (i) a first image of the target area, which is taken without the use of a contrast agent in the target area, and (ii) a second image of the target area, which is taken with the use of a contrast agent in the target area;

subtracting the second image from the first image to obtain a subtraction image;

extracting a contour of a second target from the subtraction image to obtain a contour image of the second target;

registering, based on a same marker, the contour image of the second target and a currently-acquired image; and displaying the registered contour image of the second target and the currently-acquired image in a superimposed manner, wherein the registering and the displaying the contour of the second target and the currently-acquired image comprise:

determining, based on the second image, two reference points on the contour of the second target and a mark point on the marker;

calculating a position relationship between the two reference points and the mark point;

determining, from the currently-acquired image, a corresponding mark point on the same marker;

registering the contour image of the second target and a respective currently-acquired image from among the set of currently-acquired images based on the position relationship; and superimposing, based on a relationship of the registration, the contour image of the second target separately onto the currently-acquired image and each image acquired thereafter.

12. The image presentation method for medical imaging according to claim 11, wherein the subtracting the second image from the first image to obtain the subtraction image comprises:

performing a difference calculation on the second image and the first image using a differential algorithm for digital images to obtain the subtraction image.

13. The image presentation method for medical imaging according to claim 11, wherein the extracting the contour of the second target from the subtraction image comprises:

performing detection and segmentation on the subtraction image using an edge detection algorithm and an image segmentation algorithm to obtain the contour of the second target.

14. The image presentation method for medical imaging according to claim 11, further comprising:

receiving a shift instruction for the contour image of the second target that is superimposed onto the currently-acquired image; and adjusting a position of the contour image of the second target according to the shift instruction.

15. The image presentation method for medical imaging according to claim 14, further comprising:

receiving a reset instruction for the contour image of the second target that is superimposed onto the currently-acquired image; and returning the contour image of the second target to a predetermined superimposition position according to the reset instruction.

16. An image presentation system for medical imaging, comprising:

image acquisition circuitry configured to obtain, for a target area including a first target, a first image of the target area, which is taken without the use of a contrast agent in the target area, and a second image of the target area, which is taken with the use of the contrast agent in the target area;

difference image acquisition circuitry configured to subtract the second image from the first image to obtain a subtraction image;

contour extraction circuitry configured to extract a contour of a second target from the subtraction image to obtain a contour image of the second target;

registration circuitry configured to register, based on a same marker, the contour image of the second target and a currently-acquired image; and a display configured to present the registered contour image of the second target and the currently-acquired image in a superimposed manner, wherein the registration circuitry is further configured to:

determine, based on the second image, two reference points on the contour of the second target and a mark point on the marker;

calculate a position relationship between the two reference points and the mark point;

determine, from the currently-acquired image, a corresponding mark point on the same marker;

register the contour image of the second target and the currently-acquired image based on the position relationship; and superimpose, based on a relationship of the registration, the contour image of the second target separately onto the currently-acquired image and each image acquired thereafter.

17. The image presentation system for medical imaging according to claim 16, wherein the difference image acquisition circuitry is configured to perform a difference calculation on the second image and the first image using a differential algorithm for digital images to obtain the subtraction image.

18. The image presentation system for medical imaging according to claim 16, wherein the contour extraction circuitry is configured to perform detection and segmentation on the subtraction image using an edge detection algorithm and an image segmentation algorithm to obtain the contour of the second target.

19. An image presentation system for medical imaging, comprising:
- a memory configured to store a computer program; and
- a processor configured to execute the computer program stored in the memory to cause the image presentation system to:
  - obtain, for a target area including a first target, (i) a first image of the target area, which is taken without the use of a contrast agent in the target area, and (ii) a second image of the target area, which is taken with the use of a contrast agent in the target area;
  - subtract the second image from the first image to obtain a subtraction image;
  - extract a contour of a second target from the subtraction image to obtain a contour image of the second target;
  - register, based on a same marker, the contour image of the second target and a currently-acquired image; and
  - display the registered contour image of the second target and the currently-acquired image in a superimposed manner,
  - wherein the processor is further configured to register and display the contour of the second target and the currently-acquired image by:
    - determining, based on the second image, two reference points on the contour of the second target and a mark point on the marker;
    - calculating a position relationship between the two reference points and the mark point;
    - determining, from the currently-acquired image, a corresponding mark point on the same marker;
    - registering the contour image of the second target and the currently-acquired image based on the position relationship; and
    - superimposing, based on a relationship of the registration, the contour image of the second target separately onto the currently-acquired image and each image acquired thereafter.

20. The image presentation system of claim 19, wherein the image presentation systems is part of a medical angiography X-ray machine.

* * * * *